United States Patent [19]

Coleman et al.

[11] Patent Number: 5,118,473
[45] Date of Patent: Jun. 2, 1992

[54] APPARATUS FOR DETERMINING THE CONCENTRATION OF WATER SOLUBLE SPECIES IN BIOLOGICAL FLUID

[75] Inventors: Robert L. Coleman, Framingham; Chung C. Young, Weston, both of Mass.

[73] Assignee: Nova Biomedical Corporation, Waltham, Mass.

[21] Appl. No.: 604,124

[22] Filed: Oct. 26, 1990

Related U.S. Application Data

[62] Division of Ser. No. 408,685, Sep. 18, 1989, Pat. No. 5,001,067.

[51] Int. Cl.$^5$ .................... G01N 21/01; G01N 25/20; G01N 27/416
[52] U.S. Cl. ............................. 422/68.1; 422/82.03; 422/82.05; 422/51; 436/805; 436/806
[58] Field of Search .................. 456/63, 68.1, 95, 74, 456/23, 52, 79, 71, 179, 148, 805, 806; 73/61.1 R; 422/68.1, 82.03, 82.05, 51

[56] References Cited

U.S. PATENT DOCUMENTS

4,965,049 10/1990 Lillig et al. .................... 422/68.1

OTHER PUBLICATIONS

Coleman et al., "Evidence for Formation of Bicarbonate Complexes with N$^a$ and K$^+$ under Physiological Conditions," Clin. Chem. 27: 1938-1939, (1981).
Shyr et al., "Effect of Sample Protein Concentration on Results of Analysis for Sodium and Potassium in Serum," Clin. Chem. 26: 1517 (198).

Primary Examiner—James C. Housel
Assistant Examiner—David Redding
Attorney, Agent, or Firm—Fish & Richardson

[57] ABSTRACT

An apparatus for correcting an initial measurement of the concentration of a first water soluble species dissolved in a water-based component of a biological fluid that also includes a second water soluble species and a volume occupying component, the initial measurement having been taken using an original sample of the fluid that had been diluted by an amount of additional aqueous solution to form a diluted sample is disclosed; the concentration of the second water soluble species is measured in an undiluted sample of the biological fluid to obtain a direct concentration and is measured using a diluted sample of the fluid to obtain an indirect concentration, and the initial measurement of concentration of the first species is adjusted based on a combination of the direct and indirect concentration determination of the second species. The apparatus includes a first measurement device, which may be a colorimeter or amperometer, for measuring the diluted first species concentration; a second measurement device, which may be an indirect potentiometer, for measuring the diluted second species concentration; a third measurement device, which may be an ion selective electrode, for measuring the undiluted second species concentration; in particular embodiments, additional measurement devices, which may be a gas sensor and a spectrophotometer, for measuring the concentration of species which may complex with second species, and a computer connected to the various measurement devices.

6 Claims, 3 Drawing Sheets

APPARATUS FOR DETERMINING THE CONCENTRATION OF WATER SOLUBLE SPECIES IN BIOLOGICAL FLUID

This is a divisional of copending application(s) Ser. No. 07/408,685 filed on Sep. 18, 1989, now U.S. Pat. No. 5,001,067.

BACKGROUND OF THE INVENTION

This invention relates to determining the concentration of water soluble species in a biological fluid.

Sodium and potassium ion concentrations in blood plasma, for example, can be measured directly (by direct potentiometry using an ion selective electrode) or indirectly (by flame photometry or indirect potentiometry procedures, which involve sample dilution). Methods which involve diluting the sample, however, tend to underestimate the concentration of water soluble species because the plasma water fraction of the sample (which includes the water soluble species and represents only a portion of the whole sample) is effectively diluted more than are the separate, purely aqueous, calibrating solutions used in the measurement. The effect increases with increasing protein or lipid concentration, e.g.. in pathological samples (Shyr et al., Clin. Chem. 26:1517 (1980); Coleman et al., Clin. Chem. 27; 1938-1939 (1981)).

SUMMARY OF THE INVENTION

In general, the invention features correcting an indirect measurement of the concentration of a first water soluble species dissolved in a water-based component of a biological fluid that also includes a second water soluble species and a volume occupying component, the indirect measurement having been taken using an original sample of the fluid that had been diluted by an amount of additional aqueous solution to form a diluted sample; the concentration of the second water soluble species is measured in an undiluted sample of the biological fluid to obtain a direct concentration and measured using a diluted sample of the fluid to obtain an indirect concentration, and the indirect measurement of the first species is adjusted based on a combination of the direct and indirect concentration measurements of the second species.

In preferred embodiments, adjusting the indirect measurement of the first specie includes generating a correction factor by forming a ratio of the direct and indirect measurements of the second species, the biological fluid is blood plasma or serum, the first water soluble species is glucose, and the second water soluble species is sodium ion. The blood plasma contains additional water soluble species (e.g., carbon dioxide and protein) which complex with the second water soluble species, and the correction factor is adjusted accordingly. Calculation of the correction factor (f) involves measuring a direct concentration of sodium ion in a sample of undiluted plasma, measuring a indirect concentration of sodium ion using a diluted sample, measuring the concentration of total carbon dioxide in the sample, measuring the concentration of total protein in the sample, and substituting the measured concentrations into the equation:

$$f = \frac{[Na]_d}{[Na]_i} \left( 1 + \frac{[TCO_2]}{\text{mole/l}} + \frac{[TP]}{600 \text{ g/dl}} \right).$$

The invention permits rapid, accurate determination of the concentration of. e.g., glucose in blood plasma based on indirect measurements. The correction factor accounts for fluctuations in concentration of species that interfere with the calculation of an appropriate sample dilution ratio.

Other advantages and features of the invention will become apparent from the following description of the preferred embodiment, and from the claims.

BRIEF DESCRIPTION OF DRAWINGS

We first briefly describe the drawings.

To determine indirectly the concentration of glucose in blood, a small sample of blood plasma is diluted by a known amount of water or diluent, the concentration of the glucose in the diluted sample is measured, and the measurement is adjusted by the dilution factor (the ratio of the diluted sample volume to the volume in which glucose was originally dissolved) to give the concentration of glucose in the original sample. The concentration of a species determined in this manner is known as the indirect concentration.

Figure 1:
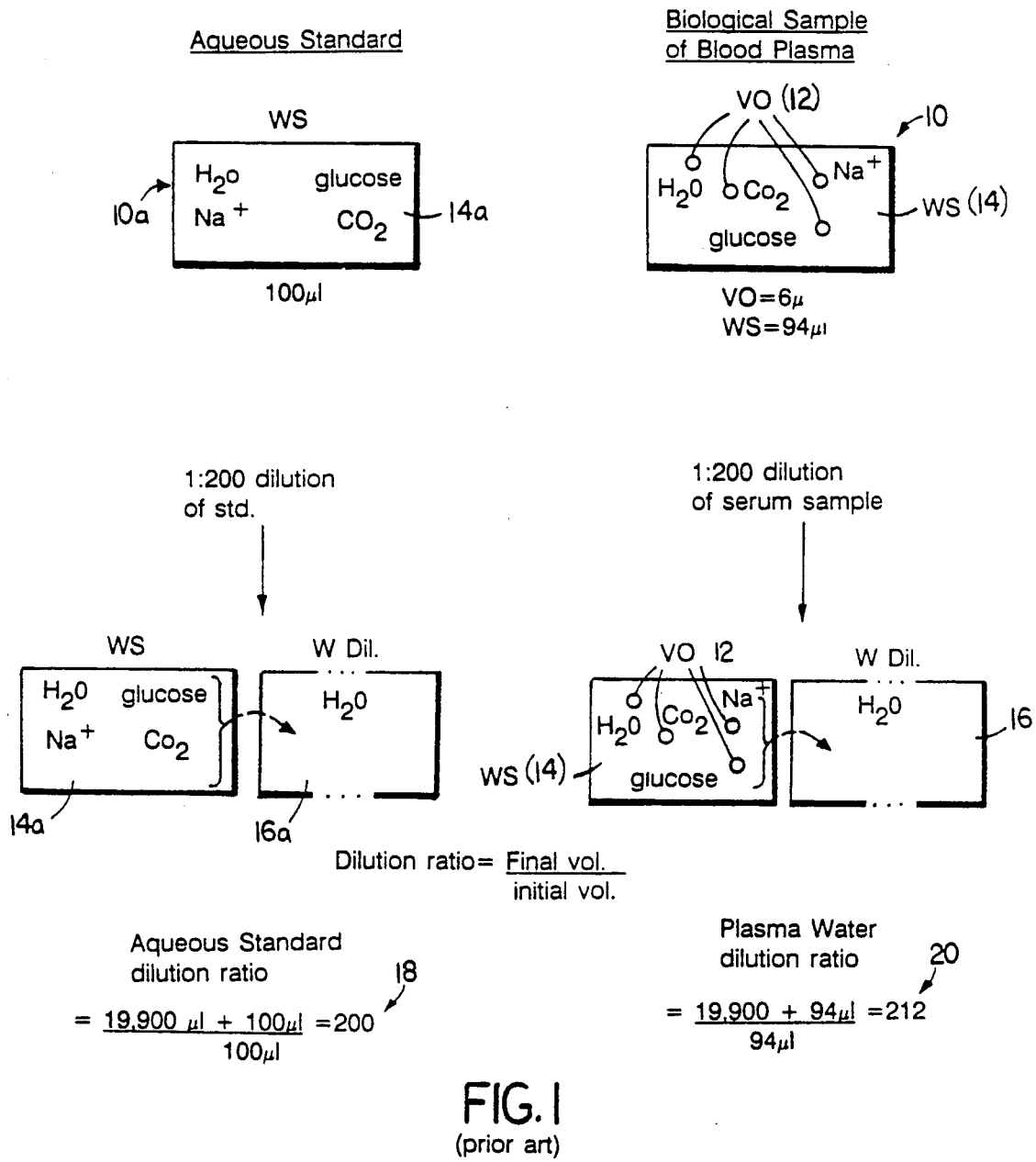
FIG. 1 is a schematic diagram of the prior art method of calculation of the plasma water dilution ratio.

Referring to FIG. 1, it can be seen that because blood plasma 10 includes a fraction 12 containing volume occupying (VO) species (e.g., lipids or the hydrophobic regions of proteins) in addition to the fraction 14 containing water soluble (WS) species (e.g., electrolytes such as sodium or potassium ions and non-electrolytes such as glucose, urea, or cholesterol), the simple ratio of diluted volume to original sample volume will not produce an accurate dilution factor for the plasma water fraction. For an aqueous standard 10a, the water soluble portion 14a is the entire sample volume of 100 μl. For a plasma sample, the fraction 12 containing VO species represents about 6% of the total volume, or 6 μl out of a 100 μl sample.

If 100 μl of aqueous standard is diluted 1:200, an aqueous standard dilution ratio 18 can be calculated as $$\frac{\text{final volume}}{\text{initial volume}}, \frac{20{,}000 \ \mu l}{100 \ \mu l} = 200.$$

A plasma water dilution ratio 20 for a sample of blood plasma, calculated in the same manner, is equal to $$\frac{19{,}900 \ \mu l + 94 \ \mu l}{94 \ \mu l} = 212,$$

or a difference of 6%. This calculation of a plasma water dilution ratio is dependent upon the ability to measure the volume VO. This volume can vary from individual to individual and can be significantly larger in pathological blood plasma samples.

A method has been developed for determining a correction factor to adjust the concentration of a water soluble species in blood plasma that eliminates the need for measuring the actual sample volume of the volume occupying fraction. Instead, a correction factor is calculated based on the ratio of direct to indirect concentration determinations for a first water soluble species (e.g., sodium ion), and that factor is used to correct the indirect concentration determination of a different water soluble species (e.g., glucose). Adjustments can be made to the correction factor to account for the formation of interfering complexes.

EXAMPLE

Figure 2:
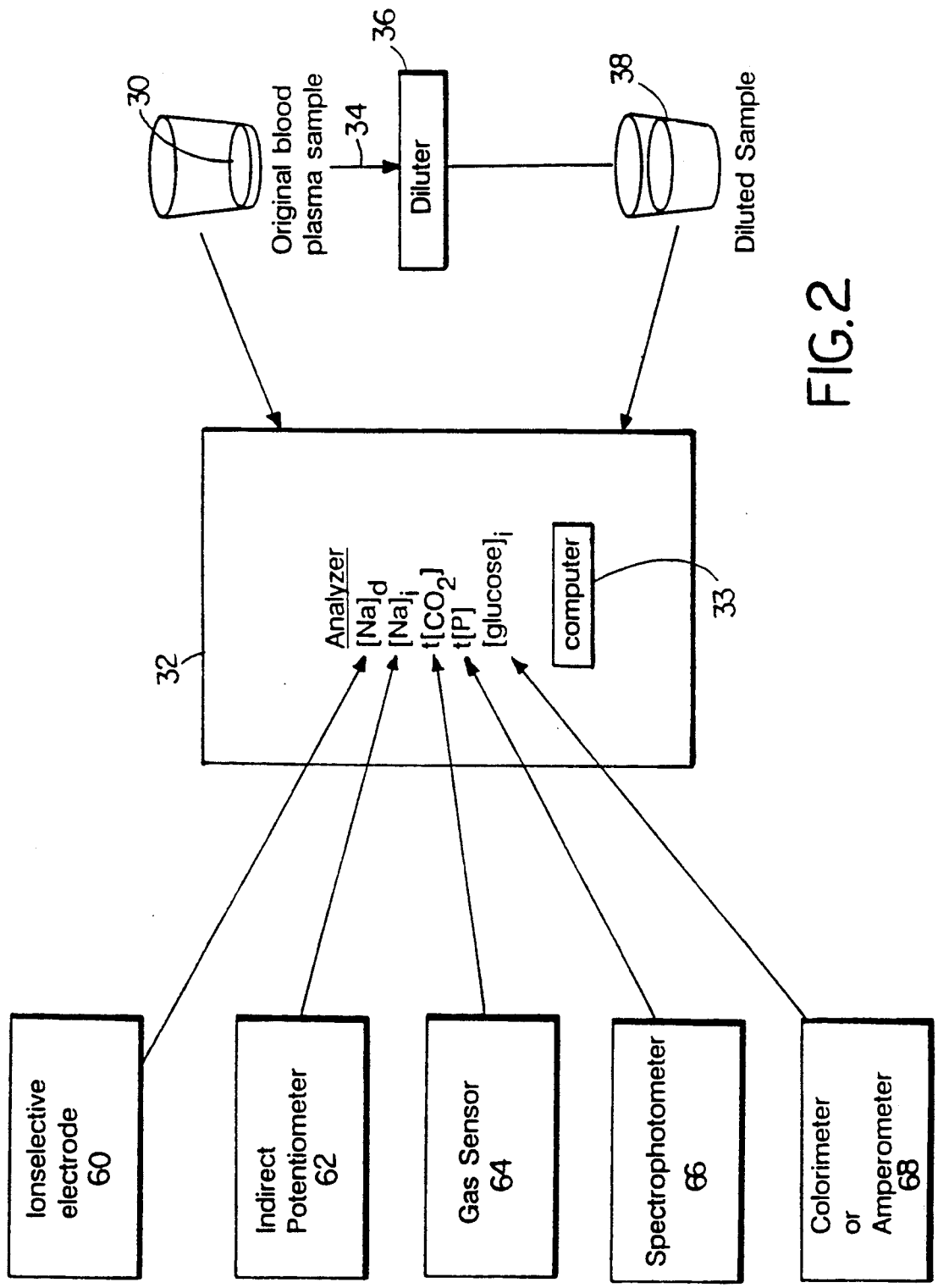
FIG. 2 is a schematic diagram of analyzer apparatus.

Referring to FIG. 2, a known volume 30 of blood plasma from a patient is placed into a sample cup and aspirated into analyzer 32. Another sample 34 of known volume of plasma from the same patient is diluted by a known amount with an aqueous solution in diluter 36, and diluted sample 38 is then also aspirated into analyzer 32.

Figure 3:
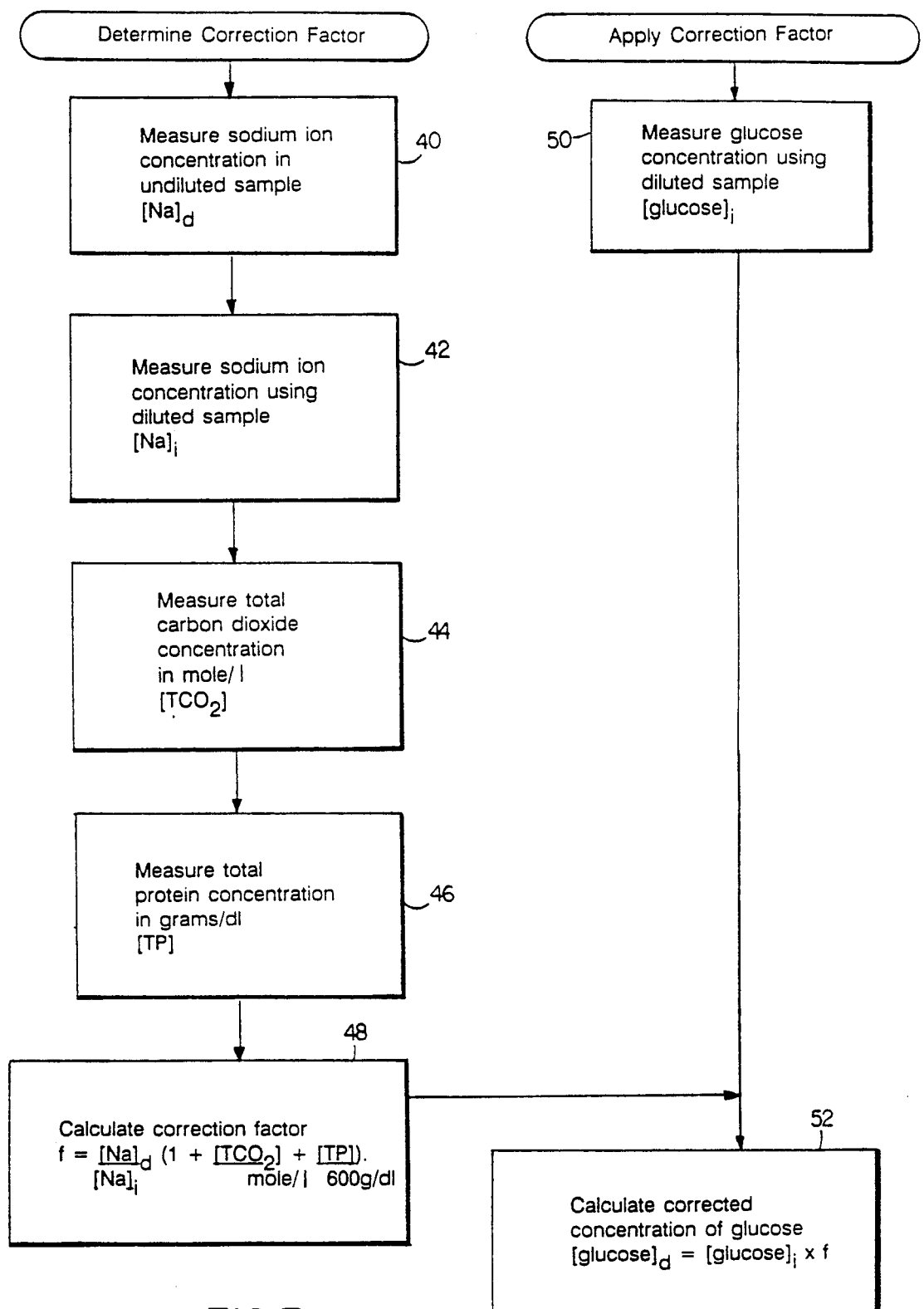
FIG. 3 is a flow diagram of a method of calculating the corrected concentration of glucose.

If sodium ion is the water-soluble species from which the correction factor is determined, adjustments to the factor must be made to correct for sodium binding to carbon dioxide (bicarbonate) and to protein. Referring also to FIG. 3, sodium concentration in the plasma is measured in the undiluted sample ($[Na]_d$ 40) by direct potentiometry with an ion selective electrode 60. Sodium concentration is measured using the diluted sample ($[Na]_i$) 42 by indirect potentiometry 62. Total carbon dioxide concentration $[TCO_2]$ 44 is measured by a gas sensor 64. Protein concentration $[TP]$ 46 is determined spectrophotometrically 66.

A plasma water correction factor is calculated, using equation 48, to be $$f = \frac{[Na]_d}{[Na]_i}\left(1 + \frac{[TCO_2]}{\text{mole}/l} + \frac{[TP]}{600 \text{ g/dl}}\right).$$

The determined values are substituted into the above equation with the following modifications: The standard units for $[TCO_2]$ are mmole/l, so the received concentration must be divided by 1000 before use. The standard units for $[TP]$ are g/dl, so the received concentration can be used directly. If the analyzer does not measure the concentration of protein, the value $[TP]$ can be set to 6 to reflect the average normal protein concentration.

Glucose concentration in the plasma sample is determined indirectly 50 using the diluted sample, by colorimetry or amperometry 68. The measured glucose concentration 50 is then multiplied by the calculated correction factor to get the corrected glucose concentration 52. Computations are performed by a computer 33 in analyzer 32 (FIG. 2).

To verify the accuracy of the correction factor, the concentration of glucose was measured directly using an enzyme electrode, in the presence of $CO_2$ (bicarbonate) and of several different concentrations of bovine serum albumin, and the measured values were compared with those obtained using the calculated correction factor to adjust the indirect measurement. The results are presented in the following table:

| Sample No. | 1 | 2 | 3 | 4 | 5 | 6 |
|---|---|---|---|---|---|---|
| BSA (g/dl) | 0 | 3 | 6 | 9 | 12 | 18 |
| bicarbonate (mM) | 20 | 20 | 20 | 20 | 20 | 20 |
| sodium direct (mM) | 137.7 | 136.1 | 135.5 | 135.2 | 134.8 | 133.7 |

-continued

| Sample No. | 1 | 2 | 3 | 4 | 5 | 6 |
|---|---|---|---|---|---|---|
| sodium indirect (mM) | 140.6 | 136.9 | 133.0 | 129.4 | 127.1 | 120.0 |
| (f) | .999 | 1.02 | 1.05 | 1.08 | 1.10 | 1.17 |
| glucose indirect (mg/dl) | 203 | 195 | 190 | 184 | 178 | 170 |
| glucose indirect × (f) (mg/dl) | 203 | 199 | 200 | 199 | 196 | 199 |
| glucose direct (mg/dl) | 202 | 201 | 202 | 201 | 201 | 200 |

It can be seen that, within experimental error, the method gives the same value as does the direct measurement of glucose concentration.

Other embodiments are within the following claims. For example, the method of calculating a correction factor to adjust indirect measurements of water soluble species is applicable to any species for which a method of indirect measurement exists (e.g., additional examples include urea, cholesterol, or lactate). Any species for which both a direct and indirect method of determination exists can serve as a reference species for calculation of the correction factor (e.g., additional examples include potassium, chloride, or even glucose). For each reference species used, appropriate adjustments must be made to the factor to reflect any complexing of the species to another water soluble species.

We claim:
1. Apparatus for determining the concentration of a first water soluble species dissolved in a water-based component of a biological fluid, said biological fluid also including a second water soluble species and a volume occupying component, said apparatus comprising
   first measurement means for measuring the concentration of said first water soluble species using a diluted sample of said biological fluid;
   second measurement means for measuring the concentration of said second water soluble species using said diluted sample;
   third measurement means for measuring the concentration of said second water soluble species using an undiluted sample of said biological fluid; and
   computer means connected to said first, second, and third measurement means for receiving the measurements therefrom and for correcting the measurement received from said first measurement means by reference to the measurements received from said second and third measurements means to obtain a corrected measurement of concentration of said first water soluble species in said biological fluid.

2. The apparatus of claim 1 wherein said computer means is adapted for calculating a correction factor based on a combination of the measurements received from said second and third measurement means.

3. The apparatus of claim 1 further comprising fourth measurement means for measuring in said biological fluid the concentration of an additional water soluble species that complexes with said second water soluble species, said computer means being connected to said fourth measurement means for receiving the measurement therefrom and for adjusting the measurement received from said first measurement means by reference to the measurement received from said fourth measurement means.

4. The apparatus of claim 2 wherein said computer means is adapted for calculating said correction factor by calculating the ratio of the measurement received from said third measurement means to the measurement received from said second measurement means.

5. Apparatus for determining the concentration of glucose dissolved in a water-based component of blood plasma having a volume occupying component, said apparatus comprising
   first measurement means for measuring the concentration of glucose using a diluted sample of said blood plasma;
   second measurement means for measuring the concentration of sodium ion in said plasma using said diluted sample, to obtain a value $[Na]_i$;
   third measurement means for measuring the concentration of sodium ion in said plasma using an undiluted sample of said plasma, to obtain a value $[Na]_d$;
   fourth measurement means for measuring the concentration of total protein in said plasma, to obtain a value $[TP]$; and
   computer means connected to said first, second, third, and fourth measurement means for receiving the measurements therefrom and for calculating a correction factor (f) as $$f = \frac{[Na]_d}{[Na]_i} \left(1 - \frac{[TP]}{600 \text{ g/dl}}\right), \text{ and}$$

for correcting the measured concentration of glucose by said factor.

6. The apparatus of claim 5 further comprising
   fifth measurement means for measuring the concentration of total carbon dioxide in said plasma, to obtain a value $[TCO_2]$, said computer means connected to said fifth measurement means for receiving the measurement therefrom and for calculating said correction factor (f) as $$f = \frac{[Na]_d}{[Na]_i} \left(1 + \frac{[TCO_2]}{\text{mole/l}} + \frac{[TP]}{600 \text{ g/dl}}\right) \text{ and}$$

for correcting the measured concentration of glucose by said factor.

* * * * *